(12) United States Patent
Porter et al.

(10) Patent No.: US 9,321,988 B2
(45) Date of Patent: Apr. 26, 2016

(54) GAS AND LIQUID TISSUE CULTURE INTERFACE

(75) Inventors: Blaise D. Porter, Minneapolis, MN (US); Philippe Levesque, Bloomington, MN (US); Jacob M. Thibodeau, Minneapolis, MN (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 1369 days.

(21) Appl. No.: 12/487,138

(22) Filed: Jun. 18, 2009

(65) Prior Publication Data

US 2010/0323438 A1 Dec. 23, 2010

(51) Int. Cl.
*C12M 1/12* (2006.01)
*C12M 1/00* (2006.01)
*C12M 1/42* (2006.01)

(52) U.S. Cl.
CPC .............. *C12M 23/38* (2013.01); *C12M 23/04* (2013.01); *C12M 29/10* (2013.01); *C12M 35/04* (2013.01)

(58) Field of Classification Search
CPC ...... C12M 23/04; C12M 23/38; C12M 29/10; C12M 35/04
USPC ..................................... 435/297.2
See application file for complete search history.

(56) References Cited

U.S. PATENT DOCUMENTS

| | | | |
|---|---|---|---|
| 3,651,607 A | 3/1972 | Lee, II | |
| 4,130,120 A | 12/1978 | Kohler, Jr. | |
| 4,485,096 A | 11/1984 | Bell | |
| 5,460,968 A | 10/1995 | Yoshida et al. | |
| 5,536,656 A | 7/1996 | Kemp et al. | |
| 5,670,708 A | 9/1997 | Vilendrer | |
| 5,763,267 A | 6/1998 | Kurjan et al. | |
| 6,632,658 B1 | 10/2003 | Schoeb | |
| 6,794,184 B1 | 9/2004 | Mohr et al. | |
| 6,979,308 B1 | 12/2005 | MacDonald et al. | |
| 7,229,820 B2 | 6/2007 | Wilson | |
| 7,270,472 B2 | 9/2007 | Carreras | |
| 7,348,175 B2 | 3/2008 | Vilendrer et al. | |
| 7,410,792 B2 | 8/2008 | Vilendrer | |
| 7,416,884 B2 | 8/2008 | Gemmiti et al. | |
| 7,472,604 B2 | 1/2009 | Moore, Jr. et al. | |
| 7,694,593 B2 | 4/2010 | Owens et al. | |
| 2001/0043918 A1* | 11/2001 | Masini et al. ................ 424/93.7 |
| 2002/0037580 A1 | 3/2002 | Schoeb | |
| 2003/0199083 A1* | 10/2003 | Vilendrer et al. .......... 435/297.2 |
| 2006/0199260 A1 | 9/2006 | Zhang et al. | |
| 2008/0113426 A1 | 5/2008 | Smith et al. | |

(Continued)

*Primary Examiner* — Michael Hobbs
(74) *Attorney, Agent, or Firm* — McCarter & English, LLP (57) ABSTRACT

An apparatus and method is described for culturing and conditioning cells on a sample. The apparatus includes a fluid delivery system that transmits gas to a first surface of a sample and transmits liquid to an opposite surface of the sample without transmitting liquid onto the first surface. Further, while culturing cells on the sample, the apparatus enables a constant or variable tension and shear stress applied to the sample. The apparatus may thus, for example, be used to culture cells on an external surface of a tissue construct with air and culture cells underneath the tissue construct with a cell growth media. The fluid delivery system may alternatively transmit liquid cell growth media underneath and on the sides of the tissue construct without flowing onto a designated external surface of the tissue construct. In this manner, cells may be cultured on the tissue construct while stretching and relaxing the tissue and further simulating a dissimilar environment on opposite surfaces of the tissue construct.

12 Claims, 12 Drawing Sheets

(56) References Cited

U.S. PATENT DOCUMENTS

| | | |
|---|---|---|
| 2008/0274545 A1 | 11/2008 | Kuo et al. |
| 2009/0000388 A1 | 1/2009 | Nickel et al. |
| 2009/0019950 A1 | 1/2009 | Dingmann et al. |
| 2009/0111180 A1 | 4/2009 | Vilendrer et al. |
| 2010/0009335 A1* | 1/2010 | Joseph et al. ............ 435/3 |
| 2010/0233811 A1* | 9/2010 | Levesque et al. ........ 435/395 |
| 2010/0255582 A1* | 10/2010 | Porter et al. ............ 435/401 |

* cited by examiner

GAS AND LIQUID TISSUE CULTURE INTERFACE

CROSS-REFERENCE TO RELATED APPLICATIONS

Not Applicable

FEDERAL SPONSORSHIP

Not Applicable

JOINT RESEARCH AGREEMENT

Not Applicable

TECHNICAL FIELD

This invention pertains generally to a system and method of culturing and conditioning cells on a sample. This invention further pertains to a culturing of cells on a sample while simulating multiple environmental conditions on select surfaces of the sample, and subjecting the sample to variable tensions, stresses, and strains.

BACKGROUND

Generally, growing or culturing cells on a tissue sample has previously been described. In the past, cells have been cultured on a selected matrix, tissue sample, vascular graft, biomedical prosthesis, substrate, medical device or other specimen. Preconditioning biological implants has been found to be beneficial in restoring function for tissue grafts, implantable biomaterials, and tissue engineered constructs. It has also been found that tissue cells cultured in dynamic environments are more likely to tolerate physiological conditions of the human body. Further, it is now recognized that it is advantageous to provide a dynamic environment that allows a constant or varying strain or other forces applied to the specimen while culturing cells on the specimen. Whether to apply a constant or varying strain is dependent upon the implant location and type of construct to develop. For example, prior to implantation, skin tissue constructs often lack the proper mechanical properties and cellular function to become fully integrated and functional. Once implanted, the skin tissue construct may routinely undergo stretching and relaxing. Restoration of the skin tissue function is more likely if the implant tissue possesses mechanical properties similar to the surrounding host tissue and if the various layers of the cells include preferred characteristics to properly integrate into host tissue.

Prior systems have seeded cells on a specimen and then subsequently supplied nutrients to the cells for growth. These systems typically either submerge the specimen in growth media or isolate opposing surfaces of the specimen by clamping around an entire perimeter of the specimen or sandwiching the specimen around the perimeter between a frame or mold. It is now recognized that it may be advantageous to restrain or grip the specimen and deliver growth media in a way that a surface and sides of the specimen may have media directed thereto, while simultaneously directing gas to an opposing surface, and further stretching or relaxing the specimen.

SUMMARY

Embodiments according to aspects of the invention include an apparatus and method for selectively delivering gases to a first selected surface of a sample, delivering liquids to an opposing surface, and delivering either gas or liquid to edges of the sample. Further, while fluids are delivered to the sample, a static, variable, or intermittent force is applied to the sample. The sample may consist of, without limitation, a harvested tissue, a tissue engineered construct (including, but not limited to skin, cornea, and lung tissue), scaffold, or other specimen (hereinafter referred to generally as a sample).

In an embodiment of the invention, liquid is delivered to a receptacle or reservoir within a chamber. A sample is suspended above the receptacle in a manner such that a lower surface of the sample contacts the liquid. The amount of liquid in the receptacle is controlled by overflows or spillways so that liquid does not overflow onto the upper surface of the sample. Inserts are placed in the receptacle to vary the liquid capacity of the receptacle. Modifying the liquid capacity facilitates applying various fluid shear stresses to the underside of the sample while using identical volumetric flow rates. Liquid that overflows from the receptacle flows into a second receptacle and, from there, drains from the chamber. Fluid ports may be used for perfusion or creating a pressure differential between the interior and exterior of the chamber. Grips retain the sample and include an adjustable separation distance between the grips to accommodate varied lengths of samples.

In an embodiment of the invention, the apparatus includes a combination gas and liquid bioreactor. The bioreactor includes a chamber; grips to retain a construct within the chamber; a fluid delivery system that transmits gases to an upper portion of the construct and transmits liquids to a lower portion of the construct; and an actuator linked to a portion of the grips to selectively provide a variable and static force on the construct. The liquid may be transmitted to the lower portion of the construct without transmitting liquid to the upper portion of the construct. Further, the fluid delivery system includes overflow controls to control a volume of liquid transmitted within the chamber. Also, a liquid capacity within the chamber is adjustable.

An aspect of the invention includes gripping a construct within a chamber to culture and condition a construct by simulating multiple environmental conditions on select surfaces of the sample, and subjecting the sample to variable tensions, stresses, and strains. A further aspect of the invention controls a volume of growth media within the chamber to selectively deliver the media to one or more surfaces of the construct while the construct is repeatedly actuated between strained and relaxed positions. A further aspect of the invention includes modulating or mitigating a condensation on a surface within the chamber.

The accompanying drawings, which are incorporated in and constitute a portion of this specification, illustrate embodiments of the invention and, together with the detailed description, serve to further explain the invention. The embodiments illustrated herein are presently preferred; however, it should be understood, that the invention is not limited to the precise arrangements and instrumentalities shown. For a fuller understanding of the nature and advantages of the invention, reference should be made to the detailed description in conjunction with the accompanying drawings.

DESCRIPTION OF THE DRAWINGS

In the various figures, which are not necessarily drawn to scale, like numerals throughout the figures identify substantially similar components.

DETAILED DESCRIPTION

The following description provides detail of various embodiments of the invention, one or more examples of which are set forth below. Each of these embodiments are provided by way of explanation of the invention, and not intended to be a limitation of the invention. Furthermore, those skilled in the art will appreciate that various modifications and variations may be made in the present invention without departing from the scope or spirit of the invention. By way of example, those skilled in the art will recognize that features illustrated or described as part of one embodiment, may be used in another embodiment to yield a still further embodiment. Thus, it is intended that the present invention also cover such modifications and variations that come within the scope of the appended claims and their equivalents.

The bioreactor of the present invention includes a chamber capable of retaining fluids within the chamber, a fluid delivery system, spaced apart grips, and an actuation system capable of repeatedly actuating the grips between multiple positions or force levels. The overall size or "footprint" of the bioreactor is designed so that the bioreactor fits within commercially available incubators. A sample of varying size and shape may be retained in the chamber between the grips. A variety of liquids (including growth media) and gases may be delivered to the sample held within the chamber to simulate a variety of natural environments the sample may encounter after implantation or during intended use. Further, the fluid delivery system delivers fluid to a select surface of the construct and the internal chamber design inhibits liquid from overflowing onto surfaces other than on the preselected surfaces. The internal chamber design also inhibits overflow of liquids while the sample is actuated between a first stretched position and second relaxed position. In this manner cells, for example, may be seeded on select surfaces of the sample and then growth media and gases may be delivered to select surfaces while the cells are cultured and the sample is stimulated by mechanical actuation and alternatively shear stresses.

The grips contained within the chamber are mechanically coupled to actuators, for example magnetic forcers, stepper motors or other motor of known suitable construction, to selectively deliver axial and linear displacement to the sample. A controller and feedback device may be utilized to control the actuators and selectively apply forces and displacements to the sample. The controller allows the user to selectively define a displacement distance or applied load on the sample. Also, the user of the apparatus may use the bioreactor to culture cells of a skin, lung, or cornea tissue while simulating the stretching and relaxing of skin, lung or cornea tissue, for example. Those skilled in the art will appreciate that it may be desired to expose one side of the skin, for example, to oxygen and carbon dioxide, while exposing the other side to cell growth media, to thereby simulate a natural environment for the skin tissue.

Figure 1:
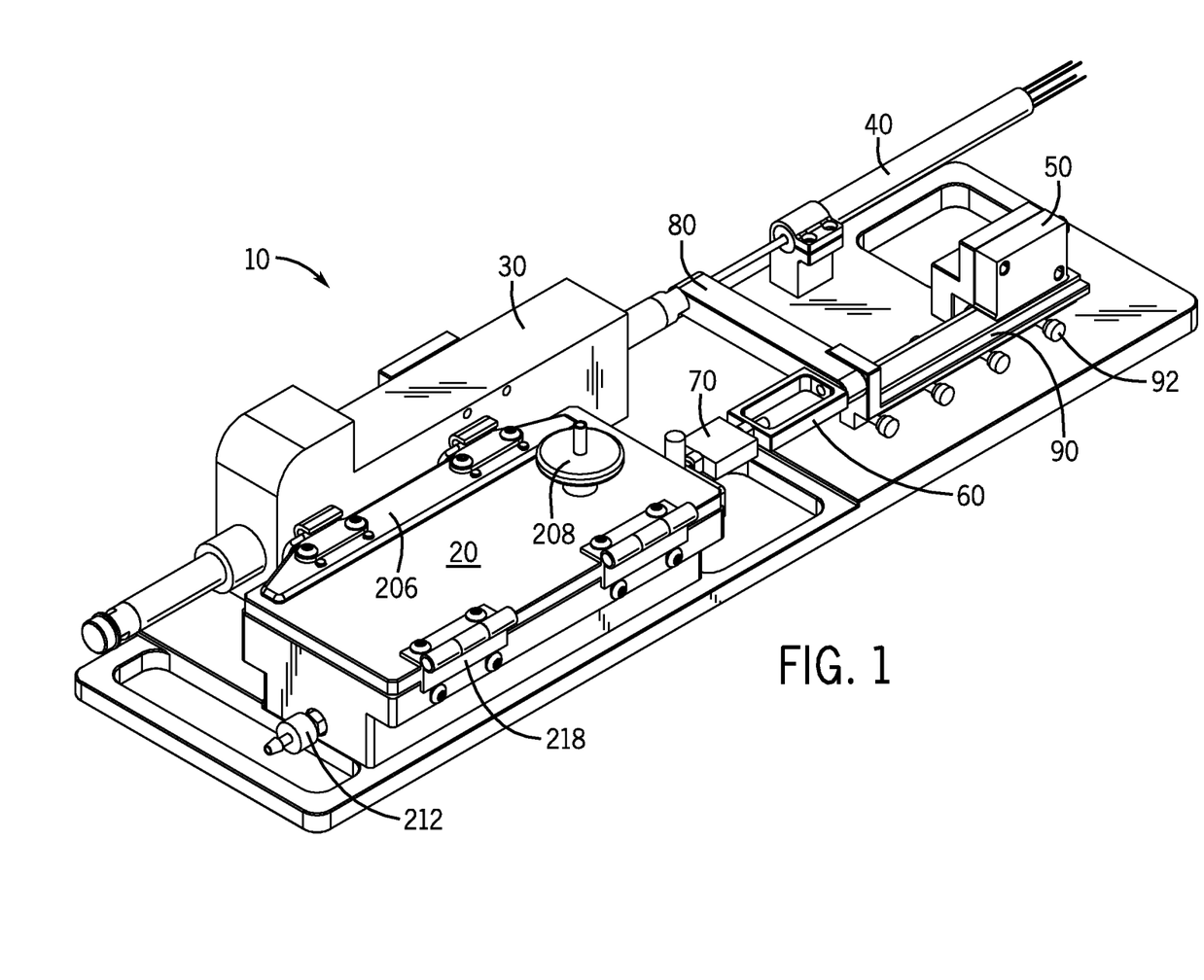
FIG. 1 is a perspective view of the bioreactor interface in accordance with an embodiment of the invention.

Turning attention now to the Figures, embodiments of the bioreactor or system 10 of the present invention will now be described in more detail. FIG. 1 generally shows the bioreactor 10 including a chamber 20, linear actuator 30, linear variable differential transformer (LVDT) 40, linear displacement transducer (LDT) 50, linkage 60, and load cell 70. Although the chamber 20 is shown in Figures as opaque, those skilled in the art will appreciate that the cover 202 and other portions of the chamber 20 may be constructed from a translucent material. The linear or axial actuator 30 is mechanically coupled to one end of a bar linkage 80 and the second end of linkage 80 is coupled to a first end of alignment linkage 60. A second end of alignment linkage 60 is coupled to a load cell 70. The load cell 70 is further coupled to a drive bar 248 which is coupled to an elbow 254 and grips 240. The first end of the alignment linkage 60 or second end of the linkage 80 may be coupled to an extender 90. The extender 90 includes rollers 92 and a magnetic strip, sensing media or other indicia associated therewith. Those skilled in the art will appreciate that an optical sensor could replace the LDT 50, however, when the bioreactor is used in humid environments sensing magnetic indicia is preferred over sensing physical markings or indicia. When the extender 90 slides under LDT 50, the amount the extender 90 (and ultimately grips 240) is displaced may be precisely determined from the LDT 50 output. The actuator 30 may be of a servo pneumatic, electromechanical flexure bearing or electromechanical linear screw motors of known suitable construction. The mechanical coupling between the various components may be aligned so that a grip 240 may be actuated fore and aft in a controlled finite manner.

A controller (not shown, but of suitable construction) may be electrically coupled to the linear actuator 30, LVDT 40, LDT 50, and load cell 70 so that feedback and analysis loops may be incorporated into the controller to selectively provide repetitive, continuous, or intermittent stimulus to a sample or construct 24 held in place between grips 240. The displacement feedback may be controlled from either or both the LVDT 40 and LDT 50 output to offset any step function observed from actuator 30 displacement. Those skilled in the art will appreciate that the redundancy with the LVDT 40 and LDT 50 may not be required for adequate function. A controller may also be utilized to control actuator 30 to thereby alter a separation distance between the grips 240 or to apply a selected load to the sample 24. A controller may further enable a user to maintain the position of the grips 240 in a fixed position to thereby translate a fixed tension on the sample 24. In this manner a variety of stimulus sequences may be applied to a selected sample 24.

It will be appreciated by those skilled in the art that setting, monitoring and controlling the separation distance between the grips enables finite control of the tension applied to the sample. Alternatively, setting, monitoring, and controlling a load on the sample allows the user to apply a consistent load on the sample independent of a particular tensile strength of the sample. Further, additional sensors may be electrically coupled to the controller to detect the position of the grips 240. The grip displacement could be measured with, by way of illustration and without limitation, an LVDT, laser PSD, incremental encoder, or other measurement feedback device of known suitable construction. Under load control, the controller adjusts the separation distance and positions of the grips 240 so that a known force (common preload) may be applied to all samples 24. The load cell 70 may also be utilized to control the force applied to the sample.

Referring now to FIGS. 2-6, the chamber 20 will be described in greater detail. The chamber 20 generally includes an enclosure 200, cover 202, latches 204, vent or cover port 208, fluid in port or conduit 210, and fluid out port or conduit 212 (see FIG. 2). The cover 202 is attached to the enclosure 200 with hinges 218 and latch extension 206 distributes the force of the latches to uniformly press the cover 202 against the enclosure 200. A perimeter seal 216 is positioned around the perimeter opening of the enclosure 200 and is sandwiched between the cover 202 and enclosure 200 to allow the user to maintain a sterile environment within the chamber 20. The lower portion of the enclosure 200 may include alignment members (not shown) to engage with the frame of the bioreactor 10, thereby fixing the chamber in place with respect to the alignment of the actuator 30, LVDT 40 and LDT 50. Ports 208 and 210 may be used to deliver fluids (either liquid or gas) into the interior of the chamber 20. Port 208 may include a valve to create a pressure differential between the exterior of the chamber and interior of the chamber 20. Further, the port 208 may include a filter therein and may be utilized to evacuate vapors from the interior of the chamber 20.

Figures 2, 6:
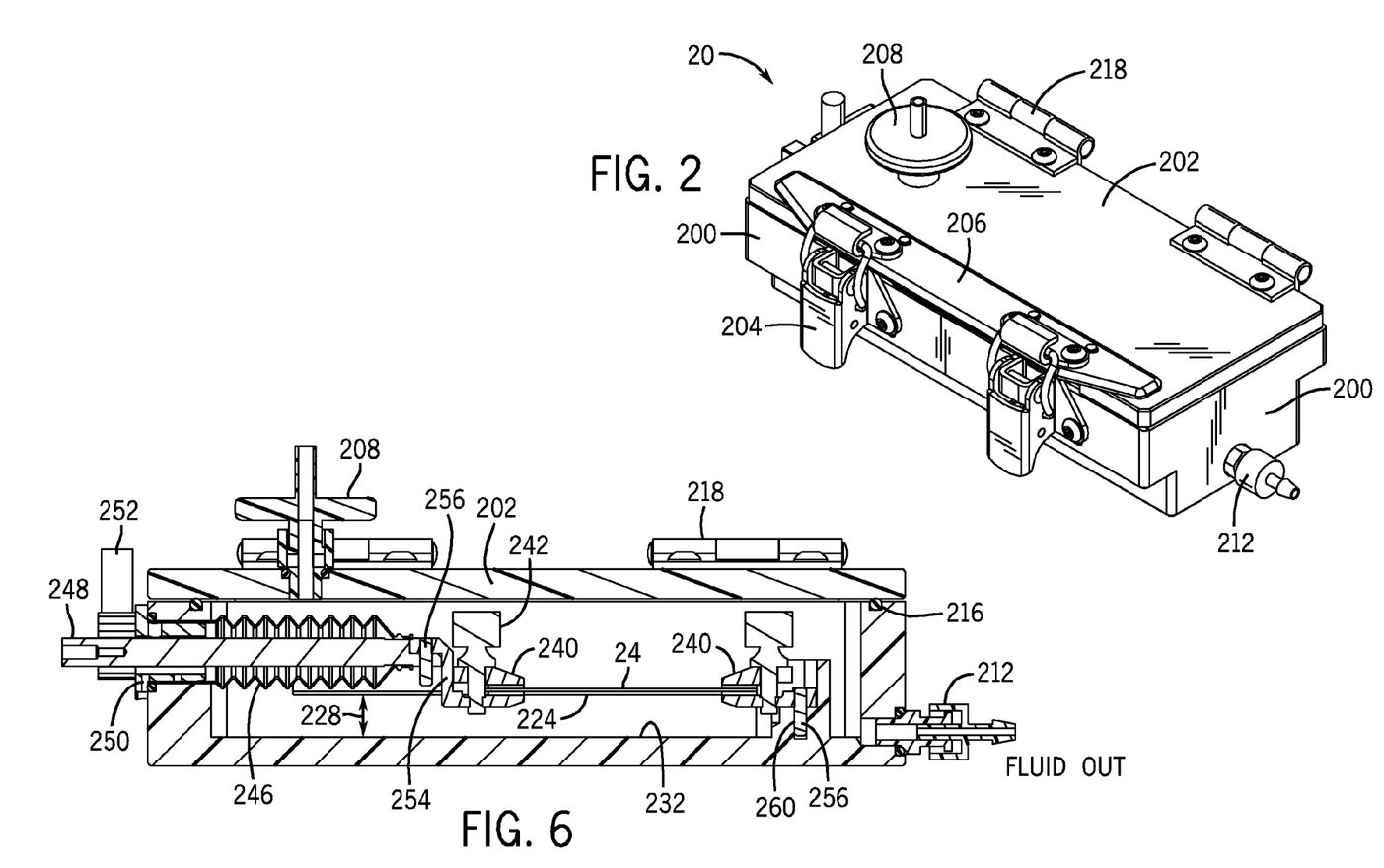
FIG. 2 is a perspective view of the bioreactor chamber of the type shown in FIG. 1.
FIG. 6 is a partial sectional side view of the bioreactor chamber of the type shown in FIG. 4, with the cover removed.
Figure 3:
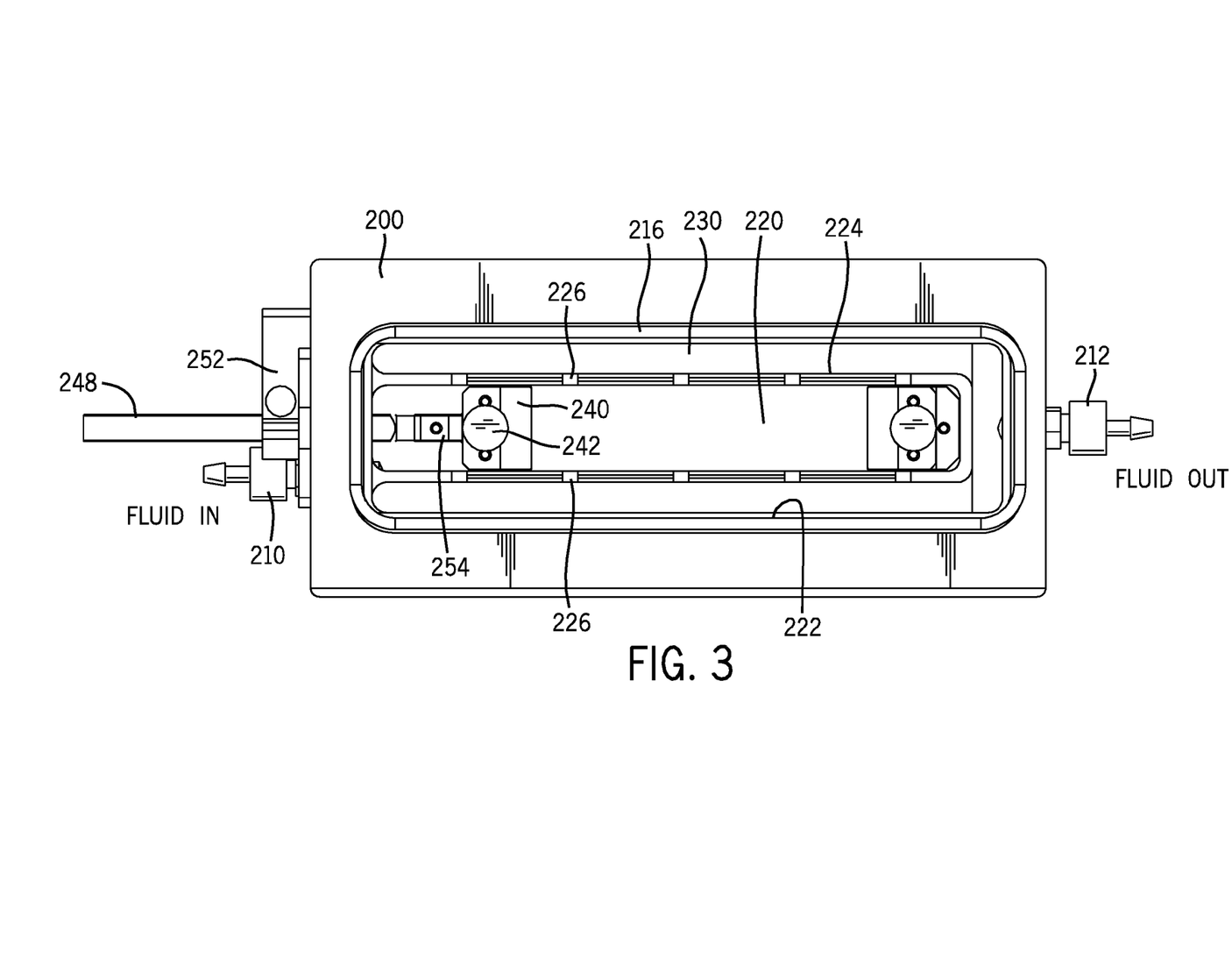
FIG. 3 is a top plan view of the bioreactor chamber of the type shown in FIG. 2 with the cover removed.
Figures 4, 5:
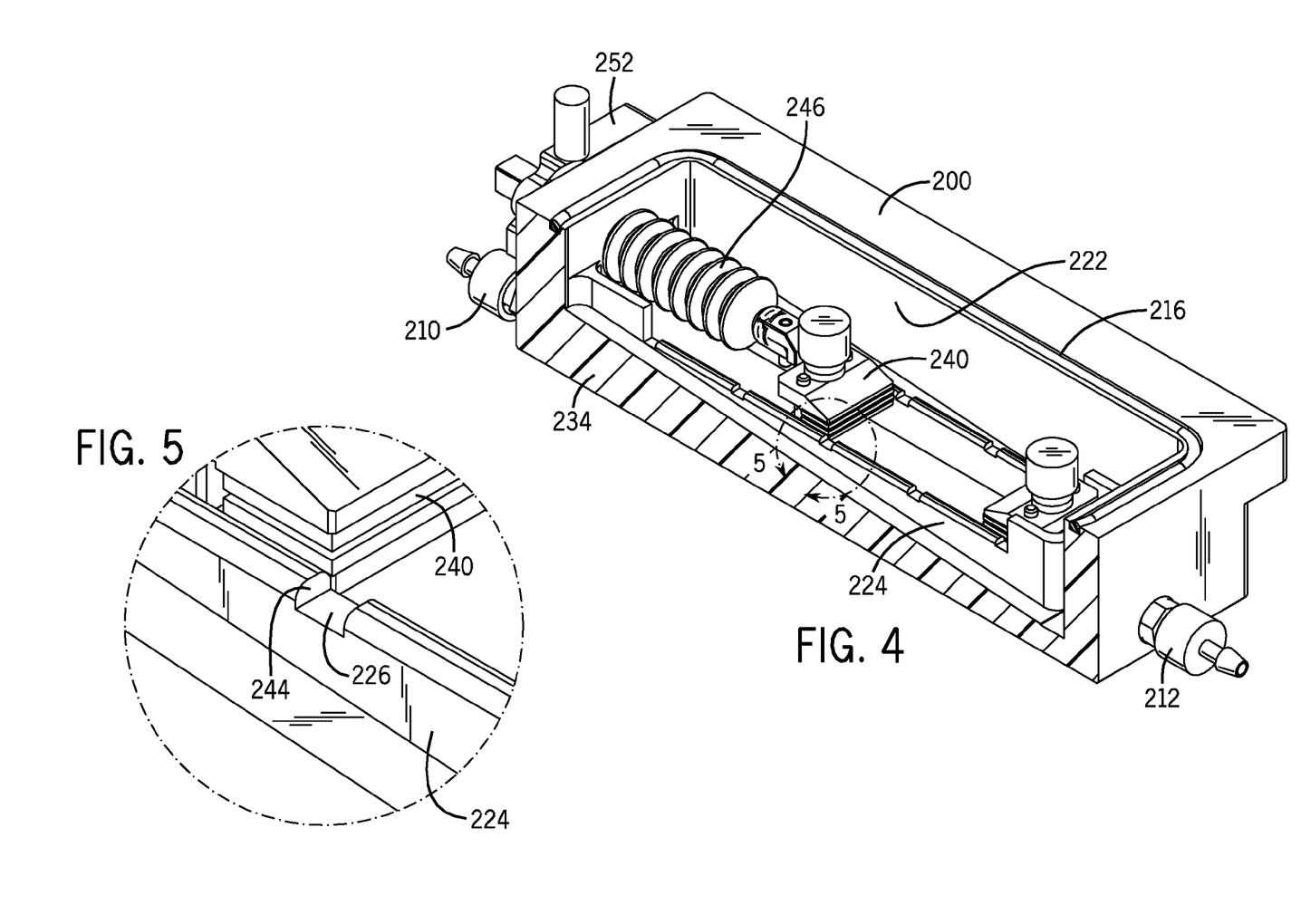
FIG. 4 is a partial sectional perspective view of the bioreactor chamber of the type shown in FIG. 2, with the cover removed.
FIG. 5 is an enlarged detail of that portion of the chamber encircled and identified as "5-5" in FIG. 4.

The interior of the chamber 20 and enclosure 200 includes an inner liquid receptacle or trough 220 and outer receptacle or trough 230 (see FIG. 3). The inner receptacle 220 includes sidewalls 224 extending from a floor 232 of the receptacle to a defined height 228 (see FIG. 6). The sidewalls 224 include one or more slots or spillways 226 that may be used to control the height of the liquid contained within the inner receptacle 220. The depth 244 of the spillway 226 defines the height of the liquid (see FIG. 5). The location of the spillway and height of the liquid affects the ability to apply fluid shear stresses to the underside of the sample. The edges of the inner receptacle 220 sidewalls 224 are rounded to further aid a uniform flow of liquid over the sidewalls and spillway 226. As the liquid reaches a height equal to the bottom of the spillway 226, the liquid overflows into the outer receptacle 230. If the flow of liquid is too great, the liquid flows through the spillways 226 and overflows over the top of sidewalls 224. The outer sidewalls 222 and slanted floor 234 of the outer receptacle 230 directs the overflow liquid to the opening of the fluid out port 212 (see FIG. 4).

Figure 7:
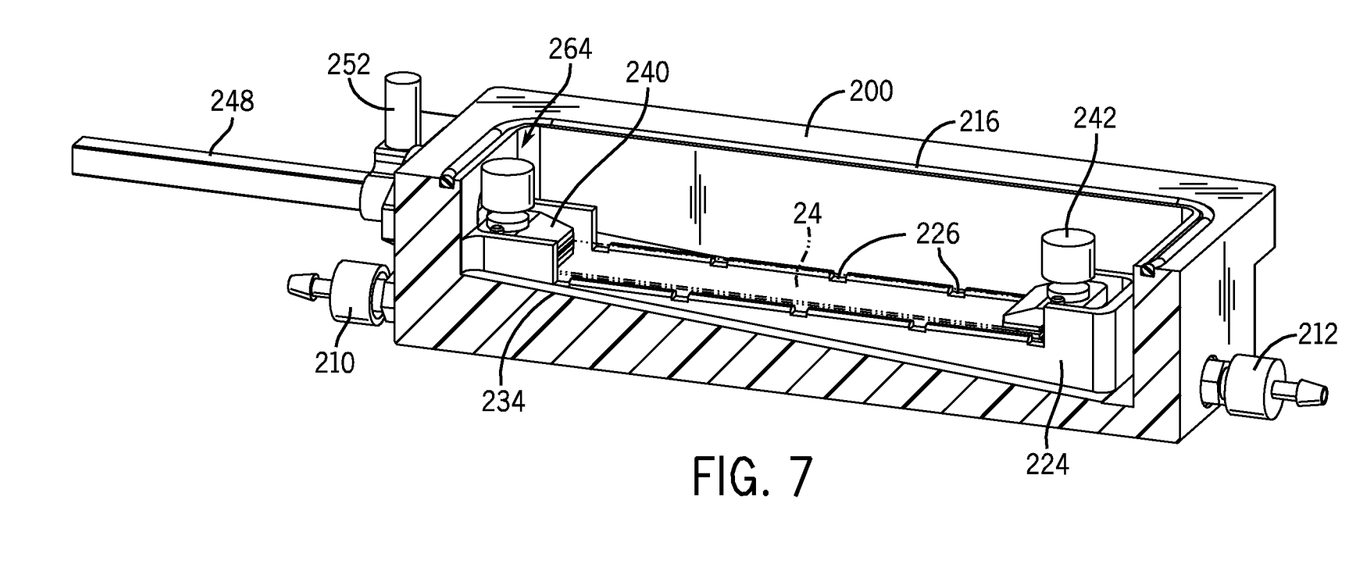
FIG. 7 is a partial sectional perspective view of the bioreactor chamber of the type shown in FIG. 4, with the cover removed, and a grip in its aft position.
Figure 8:
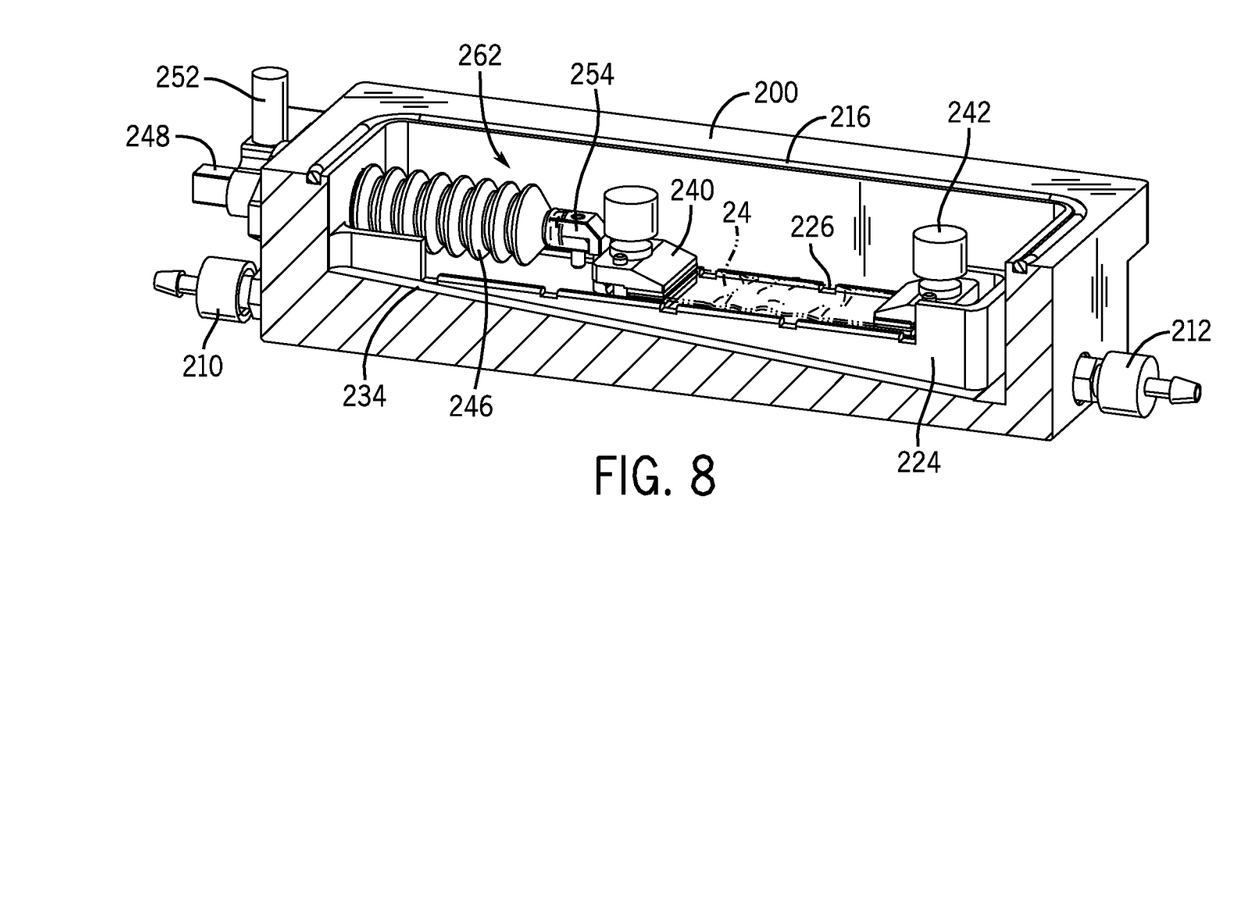
FIG. 8 is a partial sectional perspective view of the bioreactor chamber of the type shown in FIG. 4, with a grip in its forward position.

Grip 240 includes a compression knob 242 that may be turned to tighten a grip on a sample 24 sandwiched in the grip 240 (see FIG. 6). The grip 240 may include an elbow 254 to provide an offset between the center axis of the drive bar 248 and the center axis of the sample 24 positioned between grips 240. Thus, the bottom of the drive bar 248 or linear actuator is elevated above a maximum liquid level within the inner liquid receptacle. Pins 256 extend from the grip 240 and engage with apertures formed in the bottom of the spillway or in the drive bar 248. The pins 256 allow for an efficient removal and placement of the grips within the chamber 20. Drive bar 248 extends through a side of the enclosure 200 and is aligned within the chamber by drive bar guide 250. Alternatively, the guide may be oversized so that the drive bar may be angled within the guide 250. Drive bar lock 252 allows the user to adjust the separation distance between grips 240 to accommodate various lengths of sample 24. Bellow 246 surrounds drive bar 248 and a first end of the bellow 246 seals around the drive bar 248 and a second end of the bellow seals to the enclosure 200. Since the drive bar and grips include an offset, the bellows are elevated above the maximum level of liquid within the liquid receptacle and liquid is not disturbed by the bellows movement. A length of drive bar 248 that extends into chamber 20 may be controlled by controller, thus defining the maximum extension of the drive bar 248 into the chamber 20. In this manner the position of the grips 240 may be controlled when the sample 24 is in a relaxed state. When the sample 24 is stretched, the bellow and grip 240 are in the aft position 264 (see FIG. 7), and when the sample 24 is relaxed the bellow and grip 240 are in the forward position 262 (see FIG. 8). FIGS. 7 and 8 further illustrates varying lengths of sample positioned between grips 240. The sample 24 illustrated in FIG. 7 is longer than the sample illustrated in FIG. 8, and thus the position of the drive bar lock 252 varies depending upon the length of sample 24.

Figure 9:
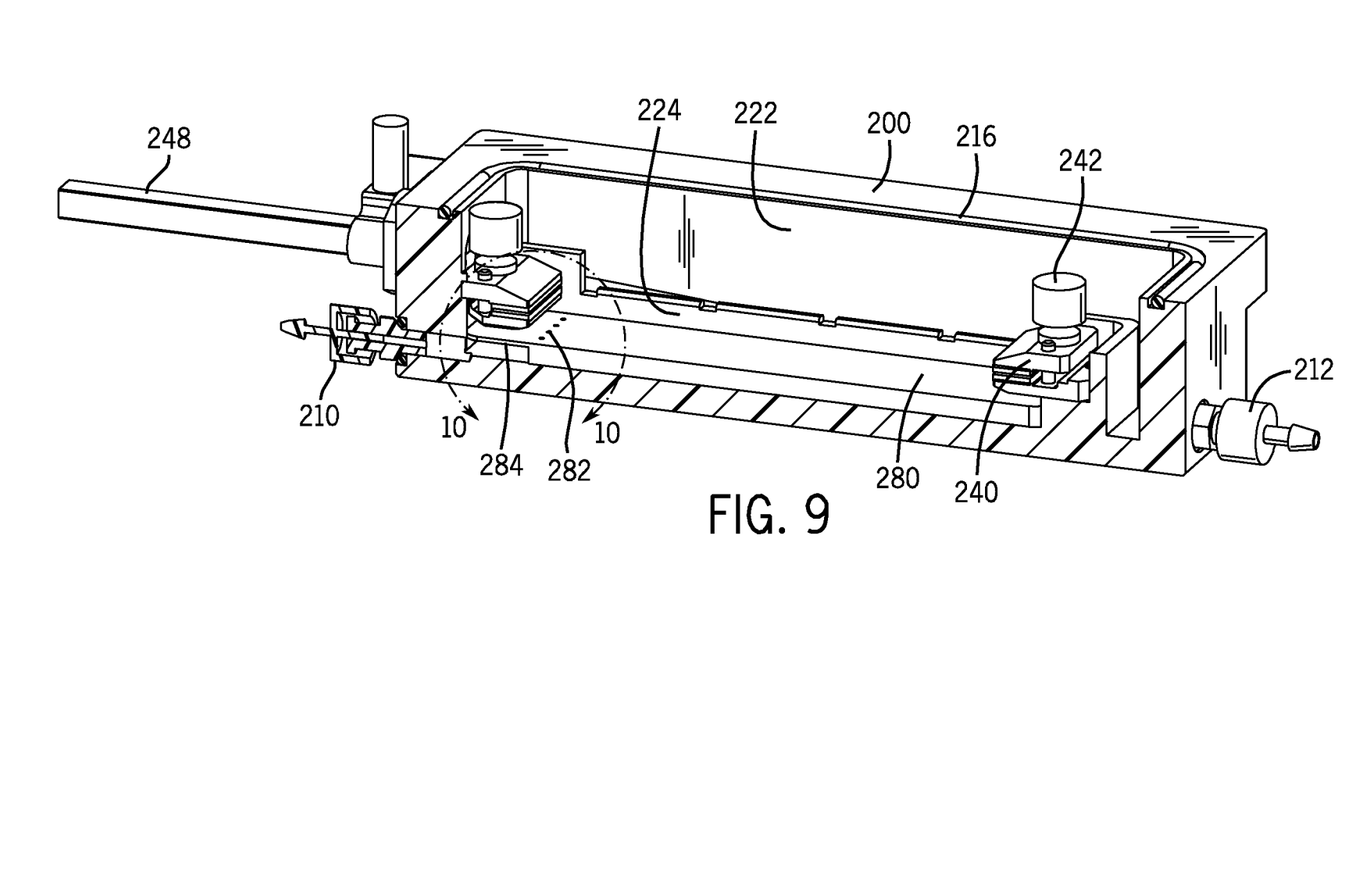
FIG. 9 is a partial sectional perspective view of the bioreactor chamber of the type shown in FIG. 7, with an insert positioned within a liquid receptacle.
Figure 10:
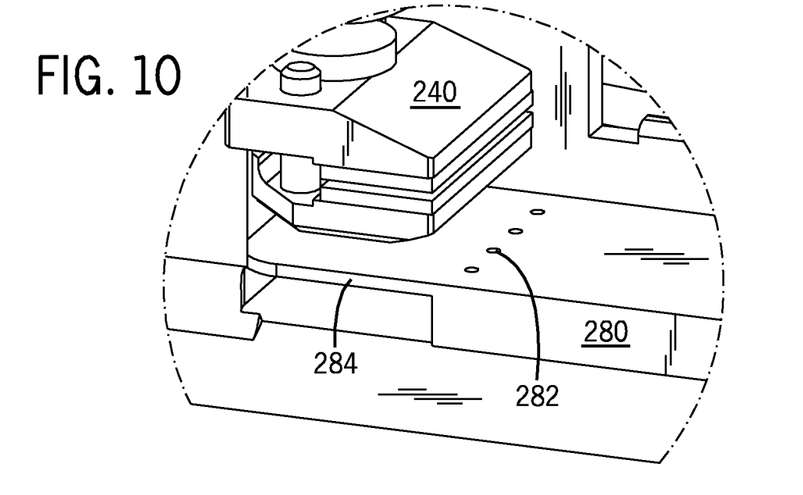
FIG. 10 is an enlarged detail of that portion of the chamber encircled and identified as "10-10" in FIG. 9.
Figure 11:
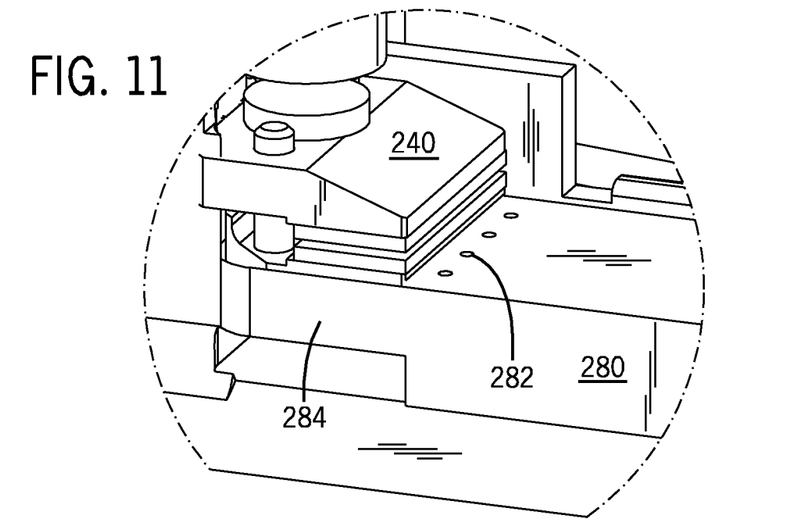
FIG. 11 is an alternate embodiment of the enlarged detail of the chamber portion illustrated in FIG. 10.

Referring now to FIGS. 9-11, an insert 280 is shown positioned within the inner receptacle 220. When positioned within the receptacle 220, the volume of fluid contained within the receptacle 220, the effective capacity of the inner receptacle, and the depth of fluid within the receptacle 220 are all reduced. An end of the insert 280 may have a varying thickness 284 (compare FIG. 10 and FIG. 11) which further affects the depth of fluid, capacity of the receptacle, and volume of liquid within the receptacle 220. By varying the depth of fluid within receptacle 220 the shear stress on the bottom surface may be modified. As the depth of fluid decreases the shear stress increases and as the depth of fluid increases the shear stress decreases. Ports 282 extend from a lower portion to an upper surface of the insert 280. The end of the insert having ports 282 is positioned near the fluid in port 210 and directs the liquid through the insert to an upper surface of the insert 280.

Having described the constructional features of embodiments of the invention, the mode of use will next be described. A user positions a selected sample 24 between grips 240. The hold of the grip 240 on the sample 24 is tightened with the compression knob 242. Liquids may be delivered through port 210 to an interior of the chamber. The fluid flows within the inner receptacle 220 until the amount of liquid exceeds the capacity of the receptacle 220 and overflows into outer receptacle 230. The relative position of the bottom surface of the sample and the height of the liquid within the receptacle 220 may be adjusted so that only the bottom surface of the sample comes into fluid communication or contact with the liquid, both the bottom and sides of the sample contact the liquid, or the bottom, top, and sides of the sample contact the liquid. While the sample is in fluid communication with the liquid, the grips may be actuated between a fore and aft position. In this manner, the sample may be subjected to a controlled stimulus including variable and static forces, fluid shear forces, as well as tension or stretching force on the sample. The actuation and/or load on the sample may be repeated as desired. Additionally, while the sample is being subjected to forces and liquids, oxygen, carbon dioxide or other selected gas may be delivered through port 208. The user may choose to deliver a variety of liquids including a growth media to assist in the culturing of the cells on the sample.

In use, the gases within the chamber 20 may have a relatively high humidity. If an external temperature is less than a temperature of the gases within the chamber, a condensation may form on an interior surface of the chamber. Further, condensation on an underside of the cover of the chamber may accumulate and form droplets. During certain uses of the chamber 20, it may be undesirable for droplets to release from the cover and fall onto a dry side of the construct 24. Without limitation, FIGS. 12-19 illustrate several alternative embodiments to mitigate or modulate a condensation within the chamber 20.

Figure 12:
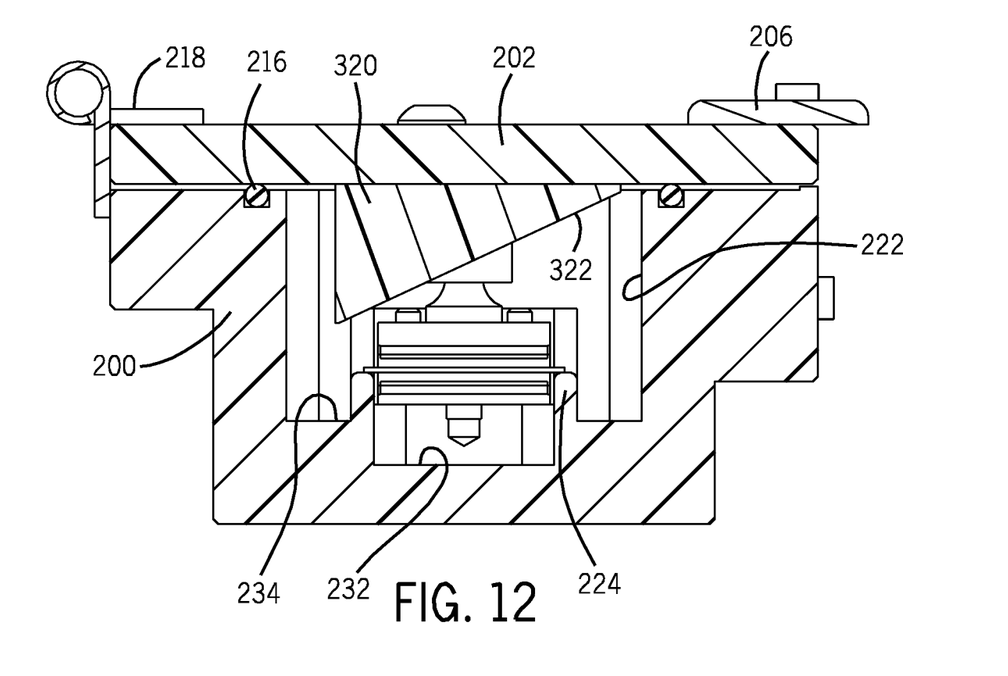
FIG. 12 is a partial sectional end view of an alternate embodiment of the bioreactor chamber of the invention.
Figure 13:
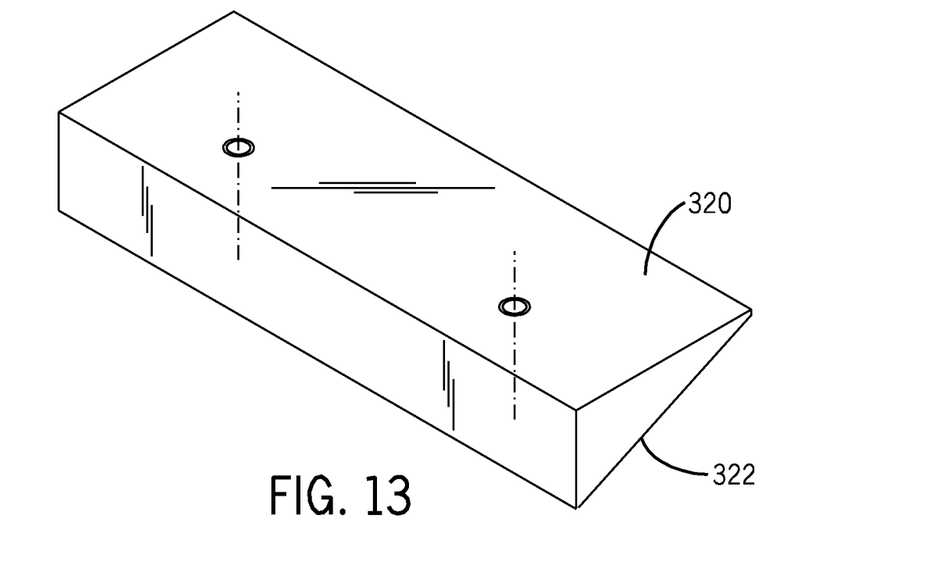
FIG. 13 is perspective of the insert of the type illustrated in FIG. 12.

With reference to FIGS. 12-13, the underside of the cover 202 of enclosure 200 may be modified to include a contoured insert 320 attached to an underside of the cover 202. The insert 320 includes a slope 322. Droplets formed on the slope tend to migrate towards the lowest point of the slope before releasing from the slope. When the droplets release, they are aligned with the outer receptacle 230 and fall into the sloped floor 234 of the outer receptacle. Those skilled in the art will appreciate that the contour and slope 322 may be formed integral to the cover rather than requiring a separate insert.

Figure 14:
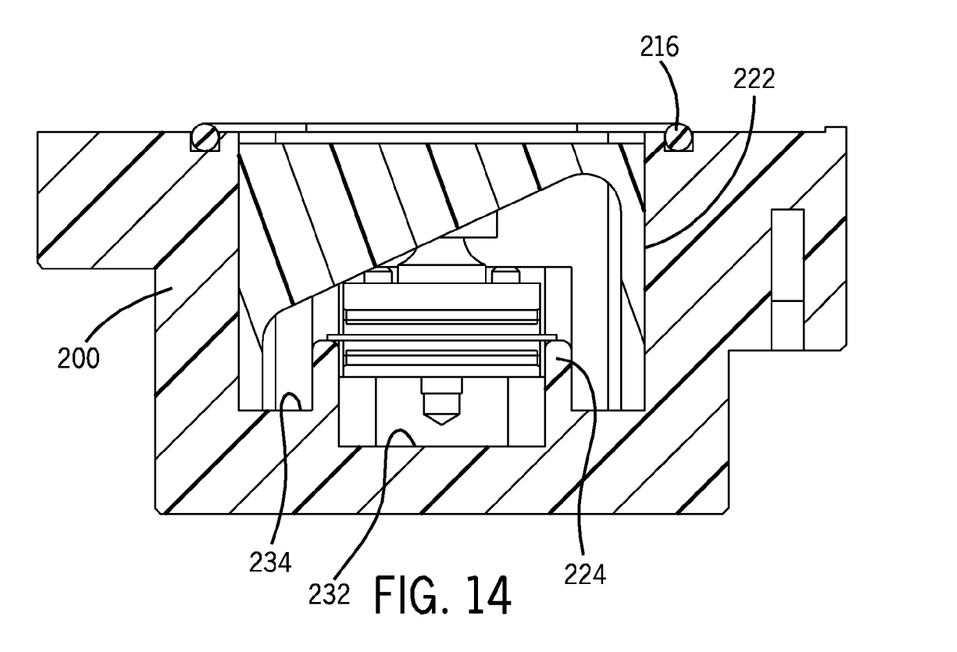
FIG. 14 is a partial sectional end view of an alternate embodiment of the bioreactor chamber of the invention.
Figure 15:
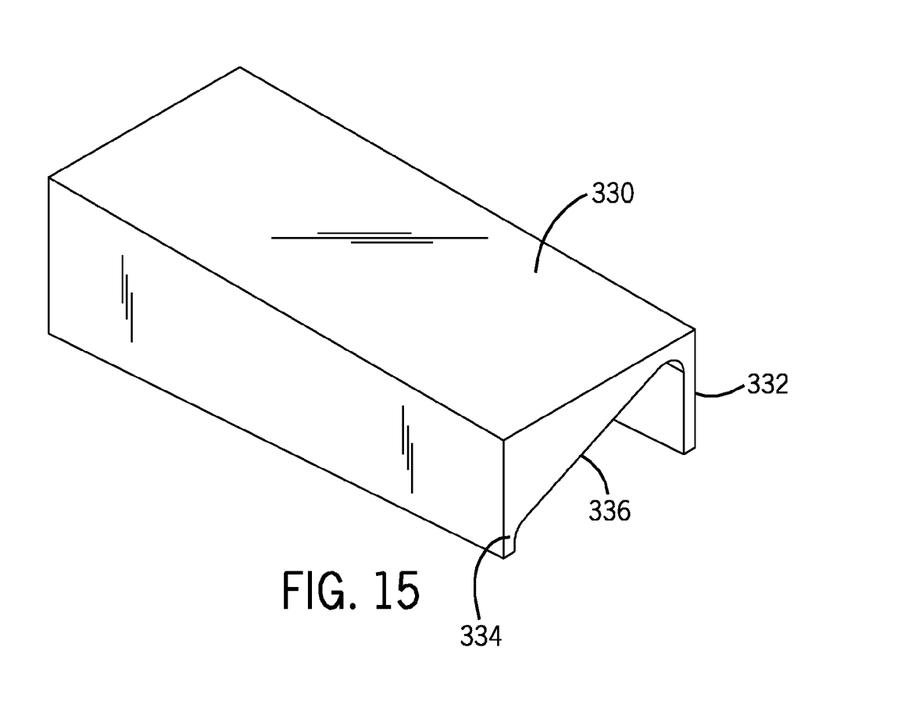
FIG. 15 is perspective of the insert of the type illustrated in FIG. 14.

Alternatively, an independent contoured insert 330 may be positioned within the chamber. The insert 330 includes flanges 332 and 334 that extend downward, the bottoms of which rest on the slanting floor 234 of the outer receptacle 230. The underside of the insert 330 includes a slope 336. Droplets formed on the slope 336 tend to migrate down the slope 336 and down pillar 334 before releasing from the insert 330. When the droplets release, they are aligned with the outer receptacle 230 and fall onto the sloped floor 234 of the outer receptacle.

Figure 16:
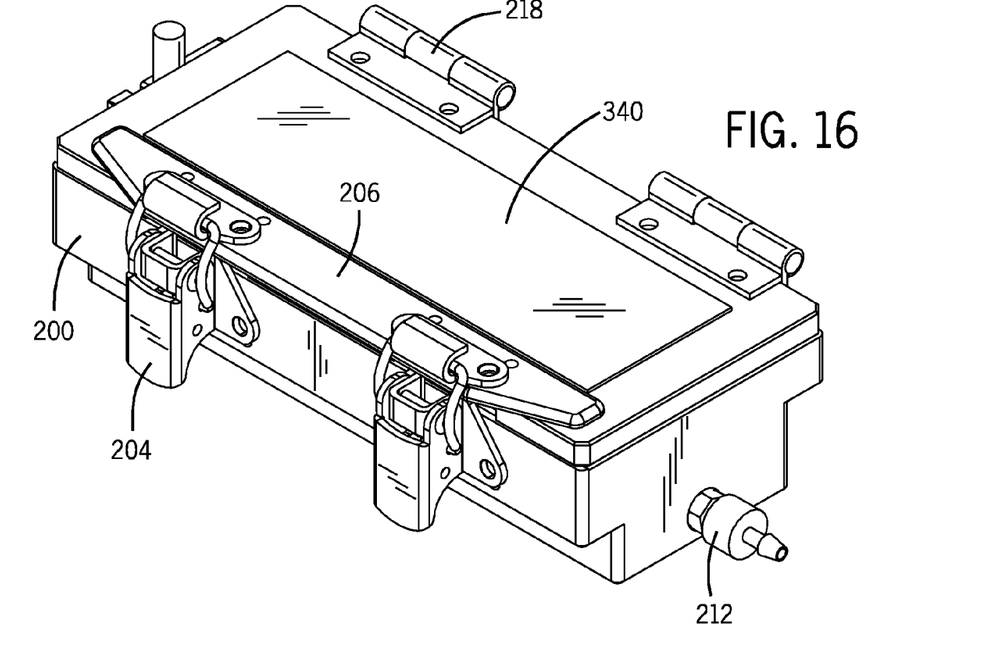
FIG. 16 is a perspective view of an alternate embodiment of the bioreactor chamber of the invention.
Figure 17:
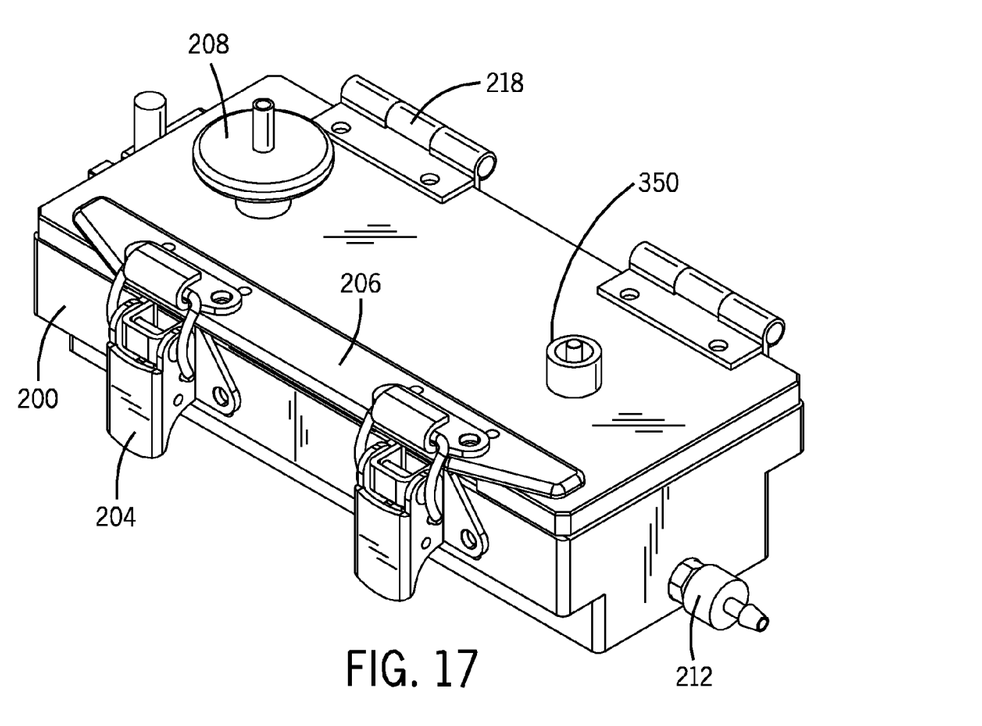
FIG. 17 is a perspective view of an alternate embodiment of the bioreactor chamber of the invention.

Shown in FIG. 16 is a modified cover that includes a filter sheet 340 formed integral with the cover. The filter 340 is of the type to allow gas vapor to pass through the filter 340 to the exterior of the chamber 20. Alternatively, as shown in FIG. 17, the cover may be modified to include a second filter or port 350. With the cover engaged to the enclosure 200 and sealed with seal 216, gases may be delivered under pressure through filter or port 208. Port 350 may function as a relief valve allowing gases to escape from the interior of the chamber once an increased pressure exceeds a desired maximum. The likelihood of condensation will decrease as the pressure within the chamber is increased. Further, a humidity of gases delivered into the chamber may be selectively controlled. Also, the temperature of the gases may be controlled by continuously porting gas at a fixed temperature into the interior of the chamber.

Figure 18:
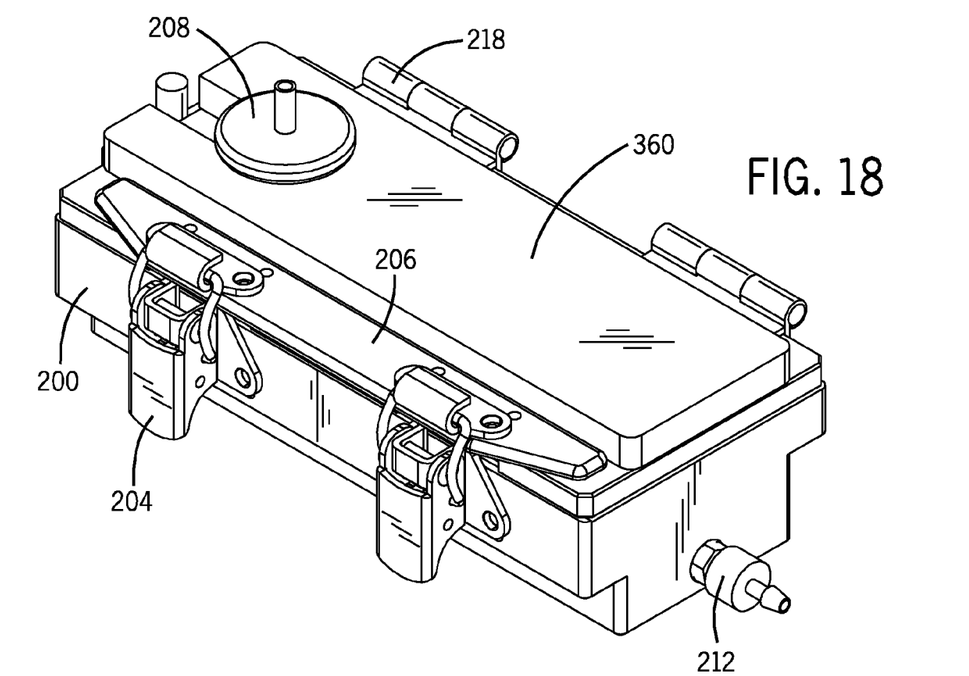
FIG. 18 is a perspective view of an alternate embodiment of the bioreactor chamber of the invention.
Figure 19:
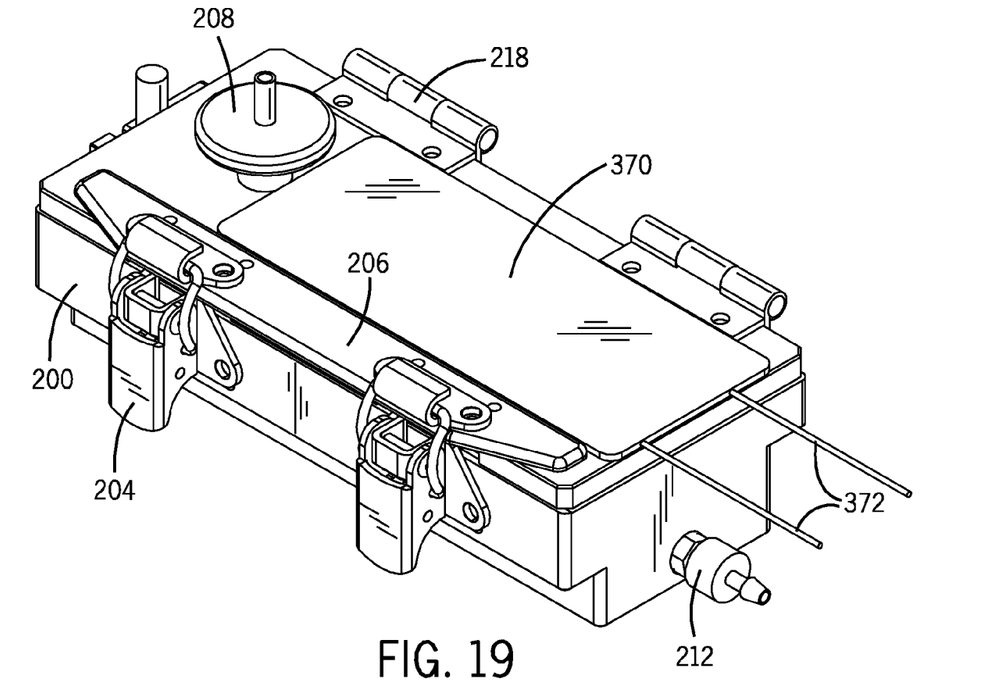
FIG. 19 is a perspective view of an alternate embodiment of the bioreactor chamber of the invention.

Alternatively, the temperature of chamber may be controlled so that condensation forming on an interior of the chamber is unlikely. Without limitation FIGS. 18 and 19 illustrate embodiments for controlling the temperature of the chamber. The chamber shown in FIG. 18 includes a plate 360 coupled to the top of the cover. The plate may be preheated or cooled, as desired, to control the temperature or compensate for the external air temperature surrounding the chamber. FIG. 19 shows a thermal pad 370 resting on an upper portion of the chamber. The thermal pad or tape 370 includes leads 372 that deliver a power supply to thermal pad. Those skilled in the art will appreciate that the pad or tape 370 may be made integral with the cover. The other components of the chamber, including port or filter 208 remain functional and operate as shown and described herein.

These and various other aspects and features of the invention are described with the intent to be illustrative, and not restrictive. This invention has been described herein with detail in order to comply with the patent statutes and to provide those skilled in the art with information needed to apply the novel principles and to construct and use such specialized components as are required. It is to be understood, however, that the invention can be carried out by specifically different constructions, and that various modifications, both as to the construction and operating procedures, can be accomplished without departing from the scope of the invention. Further, in the appended claims, the transitional terms comprising and including are used in the open ended sense in that elements in addition to those enumerated may also be present. Other examples will be apparent to those of skill in the art upon reviewing this document.

What is claimed is:

1. A combination gas and liquid bioreactor, comprising:
a chamber;
a first grip and a second grip to retain a construct within said chamber, said first grip being linearly movable within said chamber with respect to said second grip;
a fluid delivery system that facilitates gases to an upper surface and not a lower surface of the construct and transmits liquid to a lower surface of the construct without transmitting liquid to the upper portion surface of the construct, when the construct is oriented having a longitudinal axis aligned approximately parallel to a horizontal plane; and
an actuator system linked to said first grip to linearly move said first grip with respect to said second grip within said chamber, the actuator system repeatedly moving said first grip within said chamber thereby altering a separation distance between said first grip and said second grip to provide a repetitive force, a continuous force or an intermittent force on the construct during operation of the bioreactor.

2. The bioreactor of claim 1, wherein the fluid delivery system includes an overflow that controls a volume of liquid transmitted within said chamber.

3. The bioreactor of claim 2, wherein the actuator system does not disturb fluid delivery.

4. The bioreactor of claim 1, wherein a depth of liquid within said chamber is adjustable.

5. The bioreactor of claim 1, further including a port in fluid communication with an interior of said chamber, wherein said port facilitates evacuation of gas from the interior of said chamber.

6. The bioreactor of claim 1, further including a cover that encloses an interior of said chamber.

7. The bioreactor of claim 6, further including a condensation mitigator.

8. The bioreactor of claim 7, wherein said condensation mitigator includes a sloping contour of an underside of the cover.

9. The bioreactor of claim 7, wherein said condensation mitigator includes a thermal compensator.

10. The bioreactor of claim 1 wherein said second grip is attached a fixed position in said chamber.

11. The bioreactor of claim 1 wherein a position of said second grip within said chamber is free of operative engagement with said actuator system.

12. The bioreactor of claim 1 wherein said actuator system includes a drive bar movably extending through a wall of said chamber, and wherein the first grip is mounted on said drive bar.

\* \* \* \* \*